(12) United States Patent
Dahl

(10) Patent No.: US 9,888,910 B2
(45) Date of Patent: Feb. 13, 2018

(54) EYELID SPECULUM

(71) Applicant: KATENA PRODUCTS, INC., Denville, NJ (US)

(72) Inventor: Gordon Dahl, Denville, NJ (US)

(73) Assignee: KATENA PRODUCTS, INC., Denville, NJ (US)

( * ) Notice: Subject to any disclaimer, the term of this patent is extended or adjusted under 35 U.S.C. 154(b) by 254 days.

(21) Appl. No.: 14/260,141

(22) Filed: Apr. 23, 2014

(65) Prior Publication Data

US 2015/0305732 A1    Oct. 29, 2015

(51) Int. Cl.
    *A61B 17/02* (2006.01)
(52) U.S. Cl.
    CPC .......... *A61B 17/0231* (2013.01); *A61B 17/02* (2013.01); *A61B 17/0206* (2013.01)
(58) Field of Classification Search
    CPC ............ A61B 17/0231; A61B 17/0206; A61B 17/02–17/0293
    USPC .......................................................... 600/236
    See application file for complete search history.

(56) References Cited

U.S. PATENT DOCUMENTS

| | | | | |
|---|---|---|---|---|
| 4,711,240 A | * | 12/1987 | Goldwasser | A61B 17/2804 606/174 |
| 5,944,736 A | * | 8/1999 | Taylor | A61B 17/0206 600/201 |
| 6,283,913 B1 | * | 9/2001 | Seibel | A61B 1/32 600/219 |
| 6,440,065 B1 | * | 8/2002 | Hered | A61B 17/0231 600/236 |
| 2008/0108879 A1 | * | 5/2008 | Brown | A61B 17/0231 600/236 |
| 2009/0182203 A1 | * | 7/2009 | Hartnick | A61B 17/0206 600/219 |
| 2011/0077468 A1 | * | 3/2011 | Finger | A61B 1/32 600/236 |

\* cited by examiner

*Primary Examiner* — Nicholas Plionis
(74) *Attorney, Agent, or Firm* — Donald J. Lenkszus

(57) ABSTRACT

An eyelid speculum for retracting a pair of eyelids, comprises: a first arm having a first blade portion contoured to generally conform to an eyeball globe and one of the pair of eyelids; a second arm having a second blade portion contoured to generally conform to the eyeball globe an the other of the pair of eyelids; and a mechanism carrying the first arm and the second arm. The mechanism is operable to hold the first arm and the second arm parallel to and in proximity to each other so that the first blade portion and the second blade portion may be inserted between said eyelids to engage said eyelids. The mechanism is further operable to move the first arm and the second arm apart from each other while maintaining the first arm and the second arm in parallel such that the first blade portion and the second blade portion retract said pair of eyelids. The mechanism advantageously moves away from the surgical field of the eye when retracting the eyelids.

14 Claims, 5 Drawing Sheets

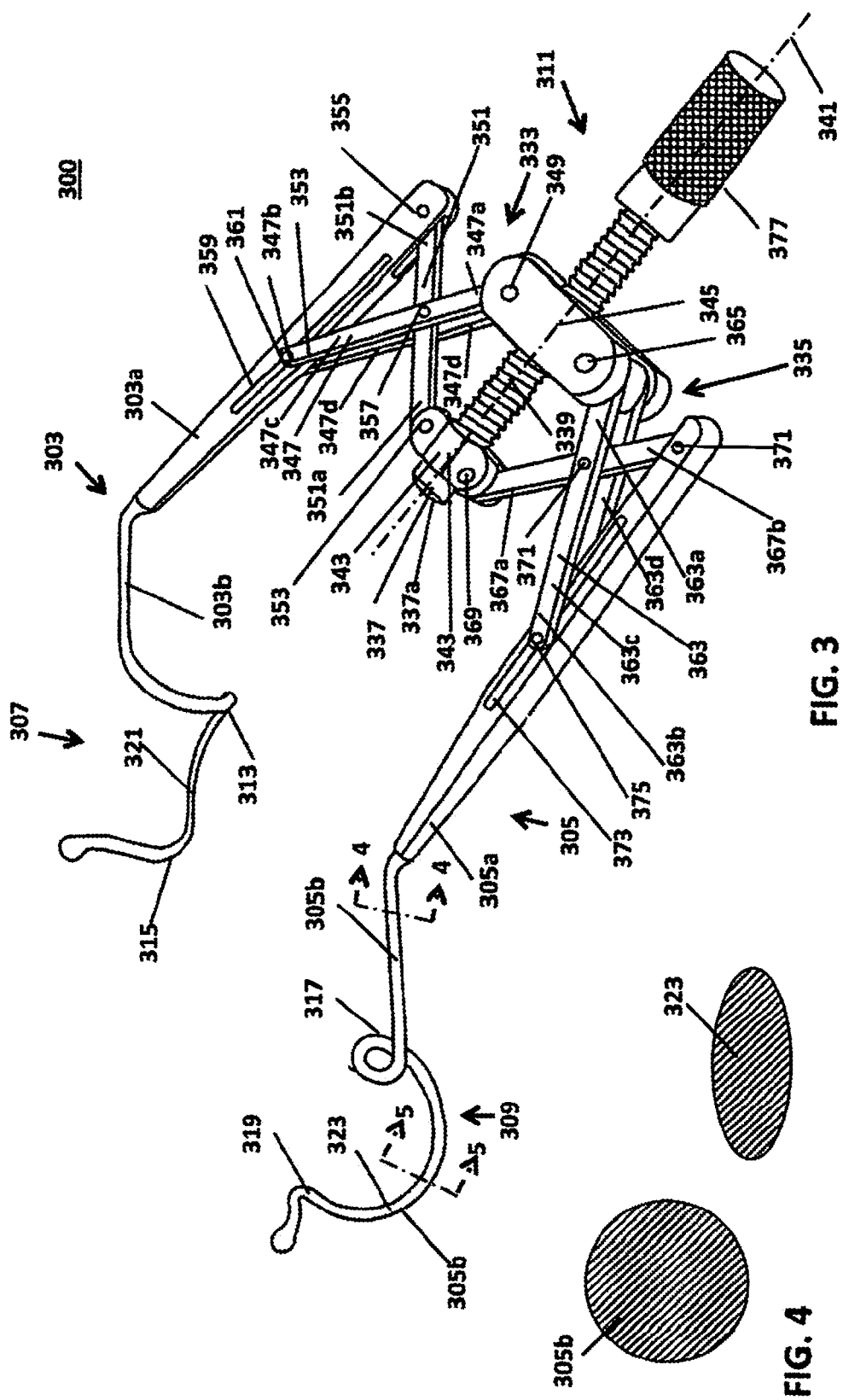

EYELID SPECULUM

FIELD

The present invention relates to an eyelid speculum device used to retract and hold open a person's upper and lower eyelids to allow access to an eye or eyeball for examination, treatment, ocular surgery, or some other reason.

BACKGROUND

In most ophthalmic procedures, a first step is to gain secure access to the surgical field in a way that is not painful to the patient. For decades this has been done with a variety of eyelid retractors commonly referred to as speculums. Speculums are usually constructed from stainless steel and have "blades" at the end of two arms, which slip underneath the eyelids. These blades are then mechanically or spring activated to open the eyelids during surgery. Since the anatomy and orbital construct of each patient is different a variety of speculums exist.

The most common speculums on the market are produced entirely from wire and are simple and inexpensive. One problem with wire speculums is that the wire weakens over time lessening the strength to keep the lids properly retracted.

Most patients are awake during cataract surgery leading to a second problem with wire speculums in that the patient has the ability to squint thereby limiting the surgical field.

Another problem is that the blades open from a single pivot point causing the lids to be retracted in a "V" shape. The part of the blade furthest from the pivot point opens wider than the end closest to the pivot point. The result is that the inferior and superior aspects of the blades are spaced apart with different distances.

A variety of mechanical speculums are on the market that attempt to both open the lids to the extent desired and to control a "squinter". Most of these speculums utilize a screw mechanism and a single pivot point to retract the lids. These speculums suffer from the same "V" shape opening problem as the wire speculums.

Cataract surgery performed with a femtosecond laser is one of the newest technologies available to eye surgeons. The unprecedented accuracy that the femtosecond laser affords a surgeon can produce better surgical outcomes and improved healing and vision for the patient.

One of the challenges to femtosecond laser technology is to provide for "docking" the laser to the patient eye. This is done through an interface device on the bottom of the laser that aspirates onto the patient's eye.

Docking is not always the easiest task since many patients have astigmatism, i.e., an irregularly shaped cornea. In addition, prior art speculums can also cause a misshapen cornea due to cornea pressure from the blades of the speculum. Cornea pressure from the blades of the speculum is a two-fold problem. First the single pivot point of prior art speculum blades causes the inferior portion of the blades to be further apart than the superior portion of the blades. Second the blades themselves are straight and press into the globe creating pressure and distortion.

SUMMARY

In accordance with the principles of the invention, an embodiment of an eyelid speculum for retracting a pair of eyelids, comprises: a first arm having a first blade portion contoured to generally conform to an eyeball globe and one of the pair of eyelids; a second arm having a second blade portion contoured to generally conform to the eyeball globe an the other of the pair of eyelids; and a mechanism carrying the first arm and the second arm. The mechanism is operable to hold the first arm and the second arm parallel to and in proximity to each other so that the first blade portion and the second blade portion may be inserted between said eyelids to engage said eyelids. The apparatus is further operable to move the first arm and the second arm apart from each other while maintaining the first arm the second elongated arm, in parallel such that the first blade portion and the second blade portion retract said pair of eyelids.

In the embodiment, the first blade portion comprises an inferior aspect and a superior aspect and the second blade portion comprises an inferior aspect and a superior aspect. The mechanism is operable to carry the first blade portion and the second blade portion in parallel relationship to each other such that the first blade portion inferior aspect and superior aspect are movable in parallel relationship to the second blade portion inferior and superior aspect, and the first blade portion inferior aspect and superior aspect are at all times each equidistant from the second blade portion inferior aspect and superior aspect.

In various embodiments of the invention, the mechanism moves away from a field proximate the eye when the speculum retracts the eyelids In various embodiments, each of the first blade and the second blade comprises a first portion adapted to be inserted underneath a corresponding one of the eyelids. Each of the first blade and said second blade first portions may have a flattened cross-section. Each of the first blade and the second blade first portions may be arcuate with a predetermined radius selected to conform to the shape of the globe of the eye.

One embodiment of an eye speculum for separating the eyelids of an eye comprises a first arm having a first blade portion at one end configured to receive one eyelid. The first blade portion comprises an inferior aspect and a superior aspect. The embodiment further comprises a second arm having a second blade portion at one end configured to receive a second eyelid. The second blade portion comprises an inferior aspect and a superior aspect. The embodiment also comprises a mechanism carrying the first arm and the second arm. The mechanism is operable to carry the first blade portion and the second blade portion in parallel relationship to each other such that the first blade portion inferior aspect and superior aspect are movable in parallel relationship to the second blade portion inferior and superior aspect, and the first blade portion inferior aspect and superior aspect are each equidistant from the second blade portion inferior aspect and superior aspect.

The mechanism may comprise a screw-actuated mechanism coupled to the first arm and the second arm and configured to carry the first arm and the second arm in parallel relationship to each other when the screw is turned.

In various embodiments, the screw mechanism comprises a lazy tong apparatus having a lead screw disposed between a first lazy tong section and a second lazy tong section. The first lazy tong section is coupled to the first arm and the second lazy tong section is coupled to the second arm.

The screw mechanism may comprise a lead screw having a first end portion and a threaded portion comprising threads, and a longitudinal axis. A first block is rotatably carried on the first end portion and a second block is rotatably carried on the threaded portion and movable longitudinally along the screw. The first lazy tong section comprises first link apparatus having one end pivotally connected to the first block and a second end in slidable engagement with the first arm, and second link apparatus having one end pivotally connected to the second block, and a second end pivotally connected to the first arm. The first link apparatus is pivotally connected to the second link apparatus. The second lazy tong section comprises third link apparatus having one end pivotally connected to the first block and a second end in slidable engagement with the second arm, and fourth link apparatus having one end pivotally connected to the second block, and a second end pivotally connected to the second arm. The third link apparatus is pivotally connected to the fourth link apparatus.

The first arm may comprise a first support arm portion comprising a first slide channel and a first pivot pin receiving hole. The second arm may comprise a second support arm portion comprising a second slide channel and a second pivot pin receiving hole. The first link apparatus second end carries a first slide pin in engagement with the first slide channel. The second link apparatus second end carries a pivot pin in engagement with the first pivot pin receiving hole. The third link apparatus second end carries a second slide pin in engagement with the second slide channel. The fourth link apparatus second end carries a pivot pin in engagement with the second pivot pin receiving hole.

The screw may comprise a third portion extending from the screw for rotating the screw.

In various embodiments each of the first blade and the second blade comprises a first portion adapted to be inserted underneath a corresponding one of the eyelids. Each first blade first portion and second blade first portion may have a flattened cross-section. Each of the first blade first portion and second blade first portion is arcuate with a predetermined radius selected to conform to the shape of the eye globe.

BRIEF DESCRIPTION OF THE DRAWING

The invention will be better understood from a reading of the following detailed description of an embodiment in which like reference designators identify like part in the various drawing figures, and in which:

FIG. 3 is a perspective view of an embodiment of a speculum in accordance with the principles of the invention;

FIG. 4 is a cross-section of the portion of the speculum of FIG. 3 taken along lines 4-4;

FIG. 5 is a cross-section of the portion of the speculum of FIG. 3 taken along lines 5-5;

DETAILED DESCRIPTION

Figure 1:
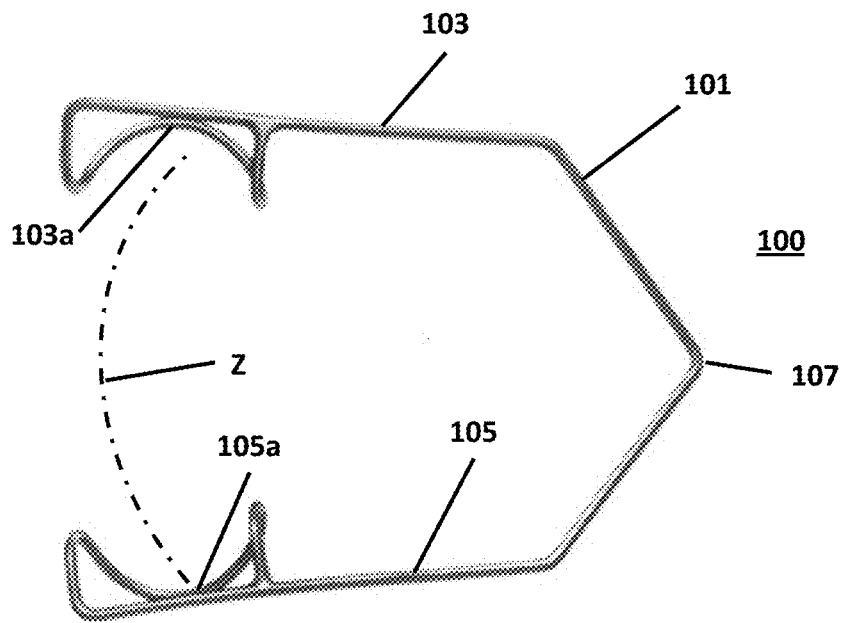
FIG. 1 is a first prior art speculum.

FIG. 1 depicts a conventional prior art eyelid speculum 100, that is used to access the eye during ophthalmic procedures by spreading the eye's eyelids. Speculum 100 comprises a single wire 101, of circular cross-section, bent to provide two arms 103, 105. Each arm at its distal end comprises a wire blade 103a, 105a to engage the eyelids of a patient. In use, arms 103, 105 are squeezed together and blades 103a, 105a are inserted under the margins of a patient's eyelids. Arms 103, 105 are released and speculum 100 returns to the open configuration shown in FIG. 1 and arms 103, 105 carry blades 103a, 105a to the position shown. In that position the eyelids, which are not shown, of the patient are spread open thereby exposing the ocular surface of the patient's eye. Because arms 103, 105 are connected at apex 107, blades 103a, 105a are carried along an arc Z as arms 103, 105 are released from the squeezed together position.

Figure 2:
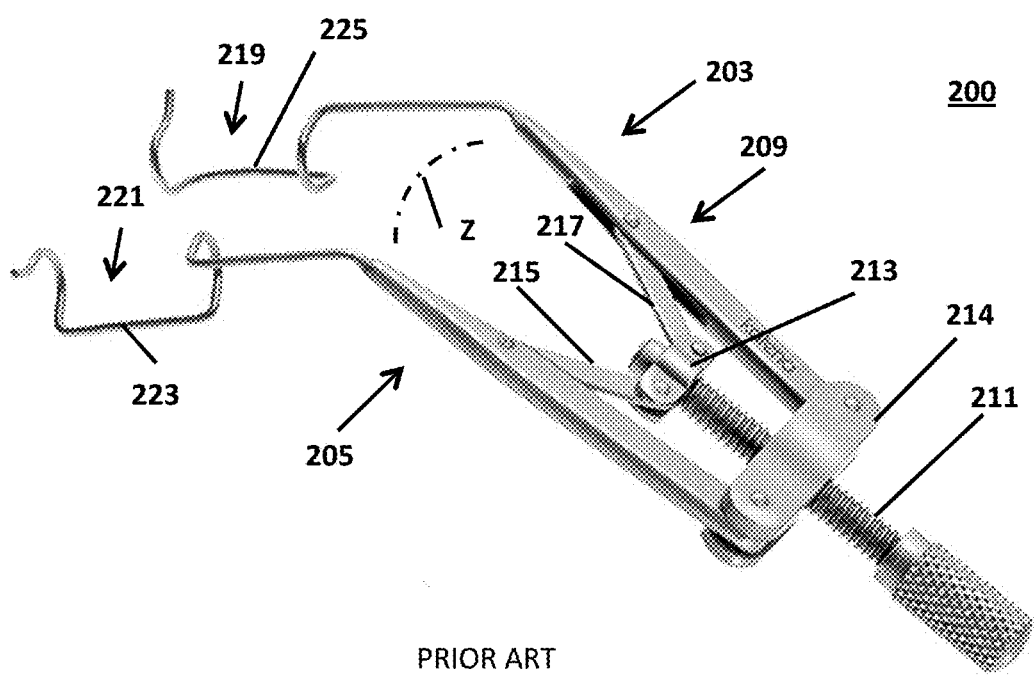
FIG. 2 is a second prior art speculum.

Another prior art speculum 200 shown in FIG. 2 has a pair of arms 203, 205 that are connected to one another by an adjusting device 209. Adjusting device 209 may be an adjustable screw mechanism having a screw 211 threaded through the center of a bridge 213. Each arm 203, 205 is pivotally attached to bridge 213 at either end of the bridge 213, and a pair of struts 215, 217 are pivotally attached to and extend from the distal end of screw 211. Each strut 215, 217 is also pivotally attached to a respective arm 203, 205 of speculum 200. Rotating screw 211 moves struts 215, 217 that in turn carry arms 203, 205. The free ends 219, 221 of arms 203, 205 may be spaced an adjustable distance from each other along arc Z. Pressure on the arms 203, 205 does not rotate screw 211. the geometry of the adjusting device 209 fixes the adjustable distance until the screw 211 is rotated.

Speculum 200 has a pair of scoops or blades 223, 225. Blades 223, 225 extend from the free end 219, 221 of each arm 203, 205, respectively. Each blade 223, 225 is generally curved or U-shaped in cross section to engage eyelids of a patient. Blades 223, 225 extend generally posteriorly or toward an eyeball from the free ends 219, 221 of arms 203, 205 when speculum 200 engages the eye of the patient A problem with both of these types of prior art speculums is that the blades 103a, 105a and 223, 225 open from a single pivot point 107, 227 causing the lids to be retracted in a "V" shape. The part of each blade 103a, 105a and 223, 225 furthest from the pivot point X 107, 227 opens wider than the end closest to the pivot point 107, 227. The result is that the inferior and superior aspects of the blades 103a, 105a and 223, 225 are spaced apart with different distances, causing the patient's eyelids to be opened in a "V" configuration.

Turning now to FIG. 3, an embodiment of an eyelid speculum 300 for retracting a pair of eyelids in accordance with the principles of the invention is shown. Speculum 300 comprises a first arm 303 and a second arm 305. First arm 303 comprises a first blade 307 contoured to generally conform to an eyeball globe and one of the pair of eyelids. Likewise, second arm 305 comprises a second blade 309 contoured to generally conform to the eyeball globe and the other eyelid of the pair of eyelids. First blade 307 comprises an inferior aspect 313 and a superior aspect 315. Second blade 309 likewise comprises an inferior aspect 317 and a superior aspect 319.

Speculum 300 also comprises a mechanism 311 carrying first arm 303 and second arm 305. Mechanism 311 is operable to hold first arm 303 and second arm 305 parallel to and in proximity to each other so that first blade 307 and second blade 309 may be inserted between said eyelids to engage said eyelids.

Mechanism 311 is further operable to move first arm 303 and second arm 305 apart from each other while maintaining first arm 303 and second arm 305, in parallel such that first blade 307 and second blade 309 retract the pair of eyelids.

Because mechanism 311 is operable to carry first blade 303 and second blade 305 in parallel relationship to each other, first blade 307 inferior aspect 313 and superior aspect 315 are movable in parallel relationship to second blade 309 inferior aspect 317 and superior aspect 319 such that first blade 307 inferior aspect 313 and superior aspect 315 are at all times each equidistant from second blade 309 inferior aspect 317 and superior aspect 319.

Mechanism 311 moves in direction X away from a field proximate the eye when speculum 300 is operated to retract the eyelids.

First blade 307 and second blade 309 each comprise a corresponding first portion 321, 323 adapted to be inserted underneath a corresponding one of the eyelids. Arm 303 comprises a first arm portion 303a and a second arm portion 303b. Likewise, arm 305 comprises a first arm portion 305a and a second arm portion 305b. Second arm portions 303b, 305b are formed from a wire or rod having a circular cross-section. The cross-section of second arm portion 305b is shown in FIG. 4. In each of first blade portion 321 and said second blade portion 323 the wire or rod has a flattened cross-section. The cross-section of second blade portion 323 is shown in FIG. 5. The flattened rod in each of first blade portion 321 and second blade portion 323 is such that first blade portion 321 and second blade portion 323 take up the least amount of space possible between the globe of an eye and the eyelids. In addition, first blade 321 and second blade 323 are each arcuate with a predetermined radius selected to conform to the shape of the globe of the eye.

Mechanism 311 comprises a screw actuated apparatus coupled to first arm 303 and second arm 305 and is configured and operable to carry first arm 303 and second arm 305 in parallel relationship to each other when a screw 331 is turned.

Mechanism 311 is a lazy tong apparatus having lead screw 331 disposed between a first lazy tong section 333 and a second lazy tong section 335. First lazy tong section 333 is coupled to first arm 303 and second lazy tong section 335 is coupled to second arm 305.

Lead screw 331 has a first end portion 337 terminating in a collar 337a. Lead screw 331 includes a threaded portion 339. Lead screw 331 comprises a longitudinal axis 341.

First end portion 337 carries a bridge or block 343 that rotatably rides on first end portion 337. A second bridge or block 345 is carried on threaded portion 339 and movable longitudinally along lead screw 331 as lead screw 331 is turned.

First lazy tong section 333 utilizes a first link apparatus 347 having one end 347a pivotally connected to second block 345 by a pivot pin 349 and a second end 347b in slidable engagement with first arm 303. First lazy tong section 333 also includes a second link apparatus 351 having one end 351a pivotally connected to first block 343 by pivot pin 353, and a second end 351b pivotally connected to first arm 303 by pivot pin 355. First link apparatus 347 is pivotally connected to second link apparatus 349 by a pivot pin 357 at the centers of first link apparatus 347 and second link apparatus 349. First link apparatus 347 comprises two links 347c, 347d that straddle second link apparatus 349 and further straddle first arm 303. First arm portion 303a has a longitudinal slot or channel 359. A slide pin 361 is carried in slot 359 by links 347c, 347d.

Second lazy tong section 335 utilizes a third link apparatus 363 having one end 363a pivotally connected to second block 345 by a pivot pin 365 and a second end 363b in slidable engagement with second arm 305. Second lazy tong section 335 also includes a fourth link apparatus 367 having one end 367a pivotally connected to first block 343 by pivot pin 369, and a second end 367b pivotally connected to first arm 303 by pivot pin 371. Third link apparatus 363 is pivotally connected to fourth link apparatus 367 by a pivot pin 371 at the centers of third link apparatus 363 and fourth link apparatus 367. Third link apparatus 363 comprises two links 363c, 363d that straddle fourth link apparatus 367 and further straddle second arm 305. First arm portion 305a has a longitudinal slot or channel 373. A slide pin 375 is carried in slot 369 by links 363c, 363d.

Lead screw 339 comprises a third portion or handle 377 extending from the screw for rotating the screw. Third portion 377 has a knurled surface to facilitate gripping the surface for rotation.

Figure 6:
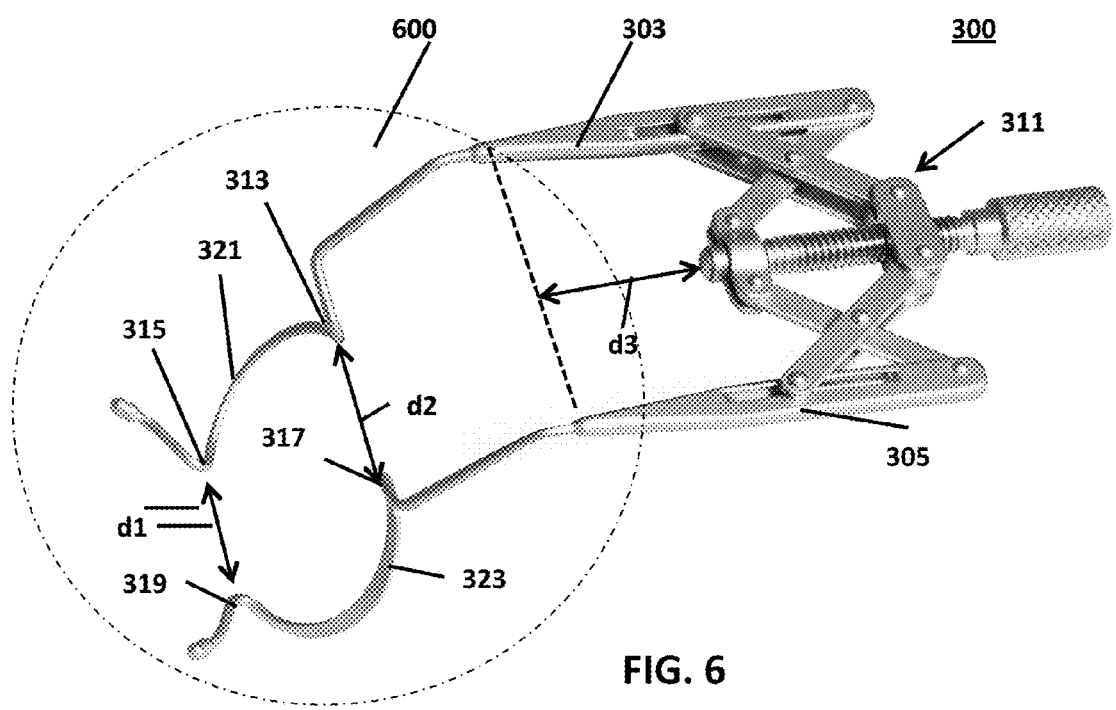
FIG. 6 is a perspective view of the embodiment of FIG. 3 in a first operable position.
Figure 7:
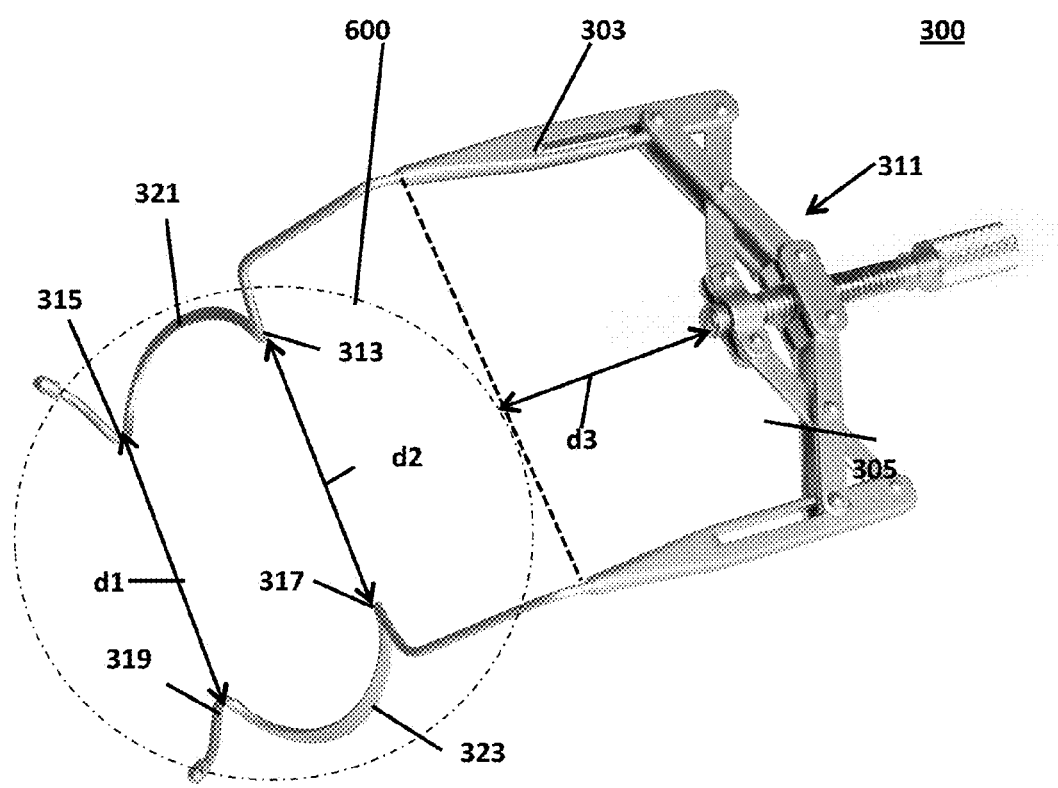
FIG. 7 is a perspective view of the embodiment of FIG. 3 in a second operable position.

FIGS. 6 and 7 illustrate how mechanism 311 moves away from the surgical field 600 as mechanism 311 is moved from an initial position shown in FIG. 6 where the eyelids are not retracted to full retraction and in FIG. 7 where the eyelids are retracted fully. In particular, the distance d3 from the surgical field 600 is greater in FIG. 7 where mechanism 311 is in the eyelid retracted position than the distance d3 in FIG. 6 where mechanism 311 is not in the eyelid retracted position. This is the opposite of the way standard mechanical speculums operate where the mechanism moves toward the surgical field and, in some instances, can hinder access.

Also shown in FIGS. 6 and 7 is that the distance d1 between superior aspects 315, 319 and distance d2 between inferior aspects 313, 321 of blades 321, 323 are equal in the first position in FIG. 6 and in the eyelid retracted position of FIG. 7.

Figure 8:
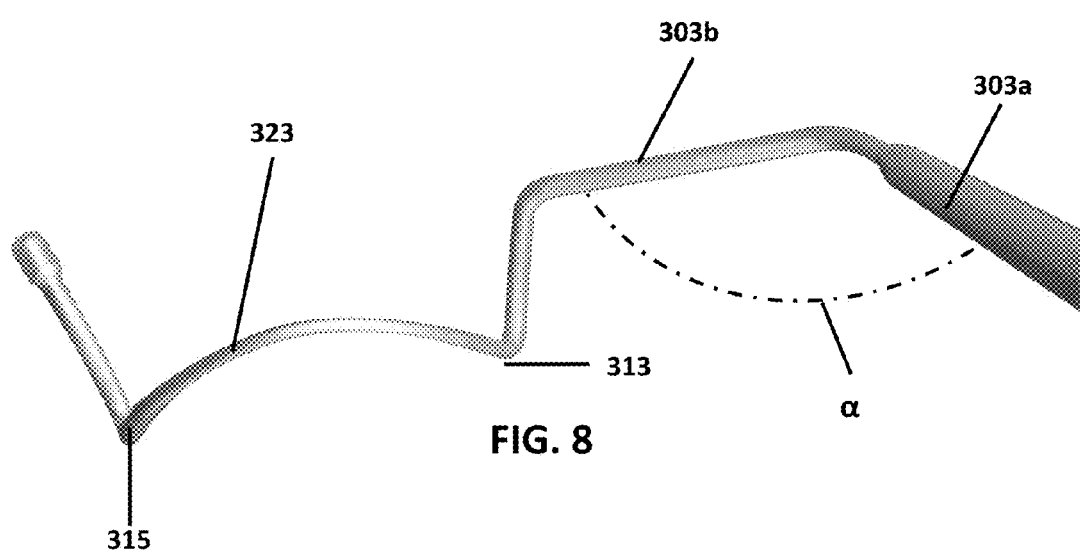
FIG. 8 is an enlarged portion of the speculum of FIG. 3.

Turning now to FIG. 8, a portion of one of the arms is shown in side view. More specifically FIG. 8 shows a portion of arm 303 is shown. One additional structural feature of speculum 300 is that arm portion 303a and arm portion 303b are not in the same plane, but are in separate planes at a predetermined angle a, which in this embodiment is 135°, with respect to each other. Advantageously by having the adjusting mechanism 311 in a separate plane from the plane defined by arm portions 303b, 305b, mechanism 311 is further removed from surgical field 600.

Preferably, the speculum 10 is constructed from one or more durable, lightweight materials that are easily formed and machined, and that may be readily sterilized. Such materials may include titanium or a titanium-based alloy, surgical stainless steel and high strength plastic, although one skilled in the art will recognize that other materials may be employed with similar effect.

The invention has been described in terms of an embodiment. It will be appreciated by those skilled in the art that various changes and modifications may be made to the embodiment without departing from the spirit or scope of the invention. It is not intended that the invention be limited by the specific embodiments shown and described. It is intended that the invention be limited in scope only by the claims attached hereto.

The invention claimed is:

1. An eyelid speculum for retracting a pair of eyelids, comprising:
   a first arm having a first blade portion contoured to generally conform to one of said pair of eyelids;
   a second arm having a second blade portion contoured to generally conform to the other of said pair of eyelids;
   said first arm and said second arm defining a first plane;
   a mechanism carrying said first arm and said second arm;
   said mechanism operable to hold said first arm and said second arm parallel to and in proximity to each other so that said first blade portion and said second blade portion may be inserted between said eyelids to engage said eyelids, said mechanism being disposed in a second plane separate from said first plane; and said mechanism comprises a screw actuated mechanism coupled to said first arm and said second arm and configured to carry said first arm and said second arm in parallel relationship to each other when said screw is turned and is further operable to move said first arm and said second arm apart from each other while maintaining said first arm parallel to said second arm when said screw is turned in a first direction and such that said first blade portion and said second blade portion retract said pair of eyelids, said mechanism moves away from a field proximate said eye when said speculum retracts said eyelids.

2. An eyelid speculum in accordance with claim 1, wherein:
said first blade portion comprising an inferior aspect and a superior aspect;
said second blade portion comprising an inferior aspect and a superior aspect;
said mechanism is operable to carry said first blade portion and said second blade portion in parallel relationship to each other such that said first blade portion inferior aspect and superior aspect are movable in parallel relationship to said second blade portion inferior and superior aspect, and said first blade portion inferior aspect and superior aspect are at all times each equidistant from said second blade portion inferior aspect and superior aspect.

3. An eyelid speculum in accordance with claim 1, wherein:
each of said first blade and said second blade comprises a first portion adapted to be inserted underneath a corresponding one of said eyelids.

4. An eyelid speculum in accordance with claim 3, wherein:
each said first blade and said second blade first portions having a flattened cross-section.

5. An eyelid speculum in accordance with claim 4, wherein:
each of said first blade and said second blade first portions are arcuate with a predetermined radius selected to conform to the shape of the globe of said eye.

6. An eyelid speculum in accordance with claim 5, wherein:
said first blade portion comprising an inferior aspect and a superior aspect;
said second blade portion comprising an inferior aspect and a superior aspect;
said mechanism is operable to carry said first blade portion and said second blade portion in parallel relationship to each other such that said first blade portion inferior aspect and superior aspect are movable in parallel relationship to said second blade portion inferior and superior aspect, and said first blade portion inferior aspect and superior aspect are at all times each equidistant from said second blade portion inferior aspect and superior aspect.

7. An eyelid speculum for separating the eyelids of an eye, comprising:
a first arm, said first arm having a first blade portion at one end configured to receive one eyelid, said first blade portion comprising an inferior aspect and a superior aspect;
a second arm, said second arm having a second blade portion at one end configured to receive a second eyelid, said second blade portion comprising an inferior aspect and a superior aspect;
said first arm and said second arm defining a first plane;
a mechanism carrying said first arm and said second arm, said mechanism being disposed in a second plane separate from said first plane, said mechanism operable to hold said first arm and said second arm parallel to and in proximity to each other so that said first blade portion and said second blade portion may be inserted between said eyelids to engage said eyelids, said mechanism operable to carry said first blade portion and said second blade portion in parallel relationship to each other such that said first blade portion inferior aspect and superior aspect are movable in parallel relationship to said second blade portion inferior and superior aspect, and said first blade portion inferior aspect and superior aspect are each equidistant from said second blade portion inferior aspect and superior aspect, said mechanism comprises a screw actuated mechanism coupled to said first arm and said second arm and configured to carry said first arm and said second arm in parallel relationship to each other when said screw is turned to separate said eyelids, said mechanism moves away from a field proximate said eye when said speculum separates the eyelids.

8. An eyelid speculum in accordance with claim 7, wherein:
said screw actuated mechanism comprises a lazy tong apparatus having a lead screw disposed between a first lazy tong section and a second lazy tong section, said first lazy tong section coupled to said first arm and said second lazy tong section coupled to said second arm.

9. An eyelid speculum in accordance with claim 8, wherein:
said screw actuated mechanism comprises:
a lead screw having a first end portion, a threaded portion comprising threads, and a longitudinal axis;
a first block rotatably carried on said first end portion; and
a second block rotatably carried on said threaded portion and movable longitudinally along said screw;
said first lazy tong section comprises: first link apparatus having one end pivotally connected to said first block and a second end in slidable engagement with said first arm; and second link apparatus having one end pivotally connected to said second block, and a second end pivotally connected to said first arm, said first link apparatus pivotally connected to said second link apparatus; and
said second lazy tong section comprises: third link apparatus having one end pivotally connected to said first block and a second end in slidable engagement with said second arm; and fourth link apparatus having one end pivotally connected to said second block, and a second end pivotally connected to said second arm, said third link apparatus pivotally connected to said fourth link apparatus.

10. An eyelid speculum in accordance with claim 9, wherein:
said first arm comprises a first support arm portion comprising a first slide channel and a first pivot pin receiving hole;
said second arm comprises a second support arm portion comprising a second slide channel and a second pivot pin receiving hole;
said first link apparatus second end carrying a first slide pin in engagement with said first slide channel;
said second link apparatus second end carrying a pivot pin in engagement with said first pivot pin receiving hole;

said third link apparatus second end carrying a second slide pin in engagement with said second slide channel; and said fourth link apparatus second end carrying a pivot pin in engagement with said second pivot pin receiving hole.

11. An eyelid speculum in accordance with claim 10, wherein:

said screw comprises a third portion extending from said screw for rotating said screw.

12. An eyelid speculum in accordance with claim 7, wherein:

each of said first blade and said second blade comprises a first portion adapted to be inserted underneath a corresponding one of said eyelids.

13. An eyelid speculum in accordance with claim 12, wherein:

each said first blade and said second blade first portions having a flattened cross-section.

14. An eyelid speculum in accordance with claim 13, wherein:

each of said first blade first portion and said second blade first portion is arcuate with a predetermined radius selected to conform to the shape of a globe of said eye.

\* \* \* \* \*